United States Patent
Blanche

(10) Patent No.: US 10,272,259 B1
(45) Date of Patent: Apr. 30, 2019

(54) HAIR GROWTH USING PHOTOTHERAPY TREATMENT

(71) Applicant: Raymond R Blanche, Chatham, NJ (US)

(72) Inventor: Raymond R Blanche, Chatham, NJ (US)

(*) Notice: Subject to any disclaimer, the term of this patent is extended or adjusted under 35 U.S.C. 154(b) by 1 day.

(21) Appl. No.: 15/917,179

(22) Filed: Mar. 9, 2018

(51) Int. Cl.
*A61N 5/06* (2006.01)
*A61B 18/20* (2006.01)
*A61B 18/00* (2006.01)

(52) U.S. Cl.
CPC .......... *A61N 5/0617* (2013.01); *A61B 18/203* (2013.01); *A61B 2018/00452* (2013.01); *A61N 2005/0647* (2013.01); *A61N 2005/0652* (2013.01); *A61N 2005/0659* (2013.01)

(58) Field of Classification Search
None
See application file for complete search history.

(56) References Cited

U.S. PATENT DOCUMENTS

| | | |
|---|---|---|
| 6,666,878 B2 | 12/2003 | Carlgren |
| 7,314,300 B1 | 1/2008 | Dorr |
| 7,722,655 B2 | 5/2010 | Lee |
| D648,858 S | 4/2011 | Hayton |
| 8,088,123 B2 | 1/2012 | Kinoshita |
| 8,192,473 B2 | 6/2012 | Tucker |
| D710,514 S | 8/2014 | Campbell |
| 9,433,773 B2 | 9/2016 | Chao |
| 9,433,774 B2 | 9/2016 | Dar |
| 2007/0129711 A1 | 6/2007 | Altschuler |
| 2010/0076529 A1* | 3/2010 | Tucker ................. A61N 5/0616 607/90 |
| 2011/0015707 A1* | 1/2011 | Tucker ................. A61N 5/0616 607/90 |
| 2011/0087310 A1 | 4/2011 | Chen |
| 2011/0251658 A1* | 10/2011 | Chen ................... A61N 5/0617 607/88 |
| 2012/0065708 A1 | 3/2012 | Kinoshita |
| 2013/0041432 A1 | 2/2013 | Tucker |
| 2013/0204315 A1 | 8/2013 | Wongsarnpigoon |
| 2015/0127072 A1 | 11/2015 | Pomar |
| 2016/0056653 A1* | 2/2016 | Tapper ................. H02J 7/0052 607/91 |

(Continued)

FOREIGN PATENT DOCUMENTS

JP S61-279257 A 12/1986

*Primary Examiner* — Erica S Lee
(74) *Attorney, Agent, or Firm* — Benjamin Appelbaum

(57) ABSTRACT

An apparatus to promote regrowth of eyebrow hair comprises a frame, and a set of temples to enable the apparatus to be worn on the forehead of a user. The apparatus includes a central member with a nosepiece, the central member being attached to one or more light hubs. Each light hub includes a plurality of light sources, and the light sources are configured to emit light onto a portion of a user's head. A head piece component attached to the central member top extends over the user's head. Light emitted by the light sources has a wavelength ranging from about 600 nanometers to about 1200 nanometers. The apparatus includes an adjustment mechanism that enables the interpupillary distance between the light hubs to be adjusted, and padding proximate the light hubs to provide a close fit between the light hubs and the user.

18 Claims, 11 Drawing Sheets

(56) References Cited

U.S. PATENT DOCUMENTS

| 2016/0106999 A1* | 4/2016 | Michaels | A61N 5/0617 604/20 |
| 2018/0021592 A1* | 1/2018 | Segal | A61N 5/0617 607/89 |

* cited by examiner

HAIR GROWTH USING PHOTOTHERAPY TREATMENT

CLAIM OF PRIORITY

This application is a United States non-provisional application that claims no priority to any previous patent or patent application.

FIELD OF THE EMBODIMENTS

This invention relates to hair regrowth technology and, in particular, to a wearable eyebrow hair regrowth apparatus.

BACKGROUND OF THE EMBODIMENTS

Hair loss affects billions of people worldwide every year. One area that is a common location that individuals experience hair loss is the head. In particular, there are many individuals who experience loss of hair in the eyebrow region. Eyebrow hair loss can be due to a multitude of reasons, including plucking of eyebrows (causing thinning), genetics, medical conditions such as alopecia areata, anagen effluvium or telogen effluvium, or the side effects from chemotherapy or other medications that result in hair loss, and other reasons.

As a result of the prevalence of eyebrow hair loss, multiple methods of restoring eyebrows, or the look of eyebrows, have been presented. These methods include coloring the eyebrow area with makeup, use of fake eyebrows, and using medications and creams to attempt to regrow the eyebrows. Many of these methods are often temporary solutions or can cause adverse effects. Therefore, for at least these reasons, a method of safely and easily restoring eyebrows of users is needed.

Examples of related art are described below:

U.S. Pat. No. 8,088,123 generally describes a hair growth modulation device that is configured to impart a suitable quantity of irradiated light to a target site while lowering the irradiation intensity required by a light irradiator that generates modulating light for modulating hair growth. This device is provided with a hair follicle approximating means that causes hair follicles of body hairs at the target site to approach the skin surface, thereby enhancing the irradiation efficiency of modulating light irradiated to the hair follicles.

U.S. Pat. No. 8,192,473 generally describes a wearable hands-free apparatus for providing phototherapy treatment to a number of hair, scalp and skin related conditions that includes a head unit (e.g., a headset, headphones, headband, or helmet unit) with earphones to allow the user to listen to an audio program during a treatment. The head unit supports a light emitting canopy band that is fitted with an array of light generating sources, such as light emitting diodes (LEDs), laser diodes, or infrared lights, that emit light within a particular wavelength range correlating with the treatment of one or more specific hair, scalp and/or skin-related conditions. The light emitting canopy band is specifically designed to conform to the shape of the human scalp for providing complete, uniform and consistent light coverage to the areas of the scalp that are most commonly affected by hair loss in men and women. A handheld control device allows the user to select the desired treatment program and is adapted for connection to a digital audio player device, such as an MP3 player, for delivering audio signals to the earphones.

U.S. Patent Publication No. 2007/0129711 generally describes a photocosmetic device for use in medical or non-medical environments (e.g., a home, barbershop, or spa), which can be used for a variety of tissue treatments. Radiation is delivered to the tissue via optical systems designed to pattern the radiation and project the radiation to a particular depth. The device has a variety of cooling systems including phase change cooling solids and liquids to cool treated skin and the radiation sources. Contact sensors and motion sensor may be used to enhance treatment. The device may be modular to facilitate manufacture and replacement of parts.

U.S. Patent Publication No. 2011/0087310 generally describes a hair restoration caring device includes a treatment hood, a suspension member and a hair caring device. The treatment hood is to be disposed over a user's head. The suspension member is fastened to the treatment hood. The hair caring device is attached to the suspension member and is movable with respect to the user scalp.

U.S. Patent Publication No. 2012/0065708 generally describes a hair-growth adjusting light emitting device that includes a device body, a light-emitting unit attached to the device body, and a locking unit for locking the light-emitting unit to the device body. The device body has a main capacitor, a device body connector, an electric power switch, a release switch, and an electric power supplying part. The light-emitting unit has a light-emitting body and a light-emitting body side connector. Furthermore, the hair-growth adjusting light emitting device includes a release restriction mechanism for preventing the light-emitting unit from being released by the release button when the electric power switch is at a power-on position where the electric power supplying part feeds the electric power to the main connector, and a power-on restriction mechanism for preventing the electric power switch from moving to the power-on position when the light-emitting unit is detached from the device body.

U.S. Patent Publication No. 2013/0041432 generally describes a device for promoting eyebrow hair growth that includes an array of light generating sources, such as LEDs, laser diodes and IPLs, which are housed within a brow plate, for providing evenly distributed light to a user's eyebrows at a low level output wavelength suitable for stimulating hair growth. This photo-biostimulation process promotes hair growth in the directed region by producing an increase in ATP and keratin production, enhancement in blood flow and circulation, as well as an increase in collagen production. Temple arm members with corresponding ear pieces or a headband are used to support the device on a user's head. The light generating sources may be powered by an internal power source, such as a rechargeable battery or disposable batteries, located within the headband or temple arm members, or by an external power source, such as a plug used in connection with an AC outlet.

Japanese Patent Publication No. JP61279257A generally describes an apparatus for promoting growth and regeneration of eyebrows that comprises an active electrode for application to the eyebrow and a dispersive electrode. A plate member supports the active and dispersive electrodes, and a flexible belt is attached to both ends of the plate member and enables the apparatus to be fitted to the patient's head. An oscillator is arranged to generate an electrotherapeutic current having a diphasic alternating potential superimposed on a pulsating current. A dc source supplies the apparatus such that the active and dispersive electrodes are energized by the electrotherapeutic current such that the potential at the active electrode is sufficiently higher than that at the dispersive electrode to effect iontophoresis of an aminovinyl photosensitizing dye.

None of the art described above addresses all of the issues that the present invention does.

Various systems and methodologies are known in the art. However, their structure and means of operation are substantially different from the present disclosure. The other inventions fail to solve all the problems taught by the present disclosure. At least one embodiment of this invention is presented in the drawings below and will be described in more detail herein.

SUMMARY OF THE EMBODIMENTS

According to an aspect of the present invention, an eye-glasses-like apparatus to promote the regrowth of hair is provided. The apparatus comprises a frame, and a set of temples to enable the apparatus to be worn on the head of a user. The apparatus includes a central member with a nosepiece, the central member being attached to one or more light hubs. Each light hub includes a plurality of light sources, such as Light Emitting Diodes ("LEDs") and the light sources are configured to emit light onto a portion of a user's head. A head piece component is attached to the central member top. Light emitted by the light sources has a wavelength ranging from about 600 nanometers to about 1200 nanometers. The apparatus includes an adjustment mechanism that enables the interpupillary distance between the light hubs to be adjusted, and padding proximate the light hubs to provide a close fit between the light hubs and the user.

It is an object of the present invention, to provide an eye-glasses-like hair regrowth apparatus, wherein one or more temples attached to the frame enable the apparatus to be worn by a user.

Another object of the present invention is to provide an adjustment mechanism that enables the interpupillary distance between the light hubs to be adjusted.

Another object of the present invention is to provide padding proximate the light hubs to provide a fit between the light hubs and the user.

It is an object of the present invention, to provide an eye-glasses-like hair regrowth apparatus, wherein the apparatus further includes a power source.

It is an object of the present invention, to provide a hair regrowth apparatus, wherein the power source is selected from the group consisting of a battery and a power cable.

It is an object of the present invention, to provide a hair regrowth apparatus, wherein the battery is a rechargeable battery.

It is an object of the present invention, to provide a hair regrowth apparatus, wherein the light emitting devices are configured to emit light at a wavelength suitable for promoting regrowth of hair.

It is an object of the present invention, to provide a hair regrowth apparatus, wherein the light emitting devices are light emitting diodes.

It is an object of the present invention, to provide a hair regrowth apparatus, wherein the apparatus is configured to fit over a forehead portion of the head of a user.

DETAILED DESCRIPTION OF THE INVENTION

Figure 1:
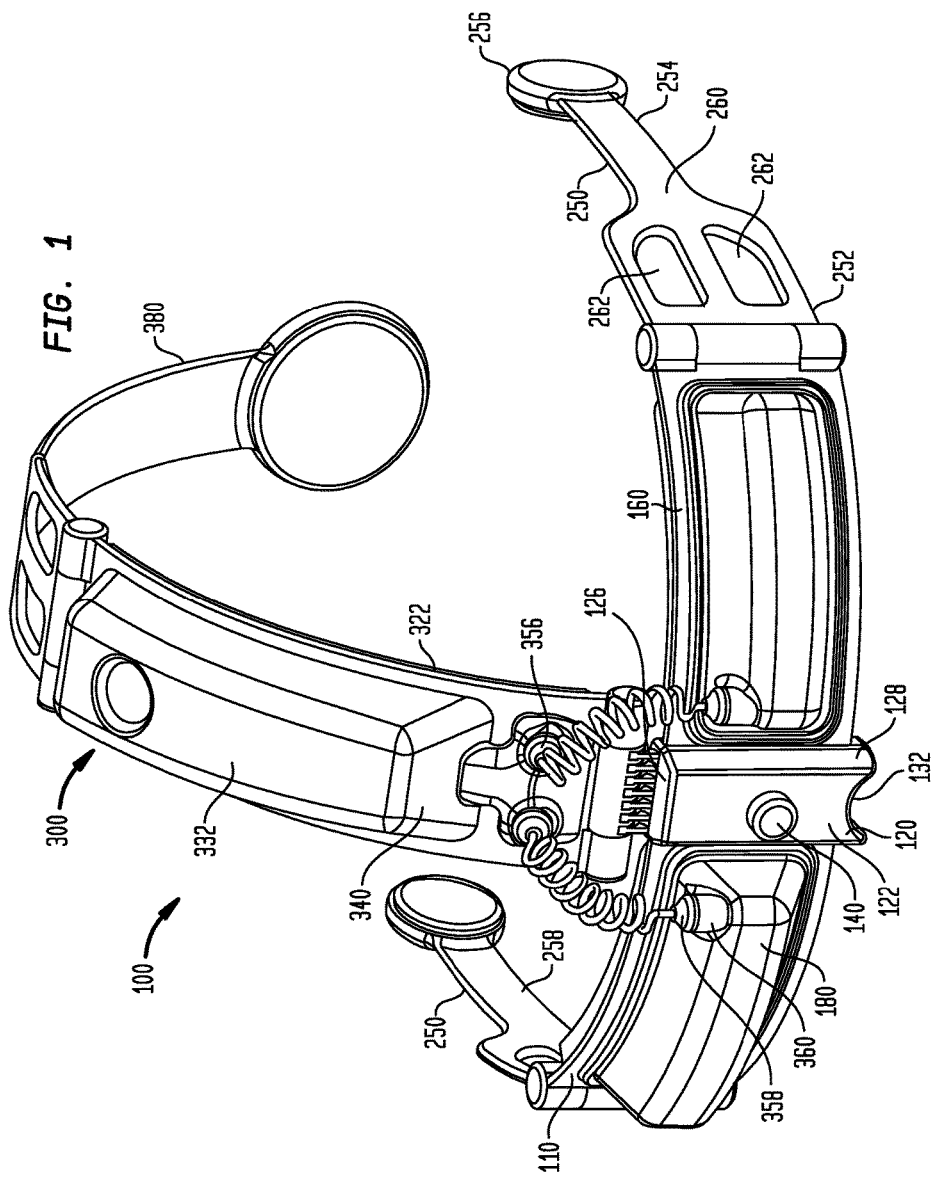
FIG. 1 shows a side perspective view of an embodiment of the eye-glasses-like eyebrow hair regrowth apparatus, in an open position.

Embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Figure 2:
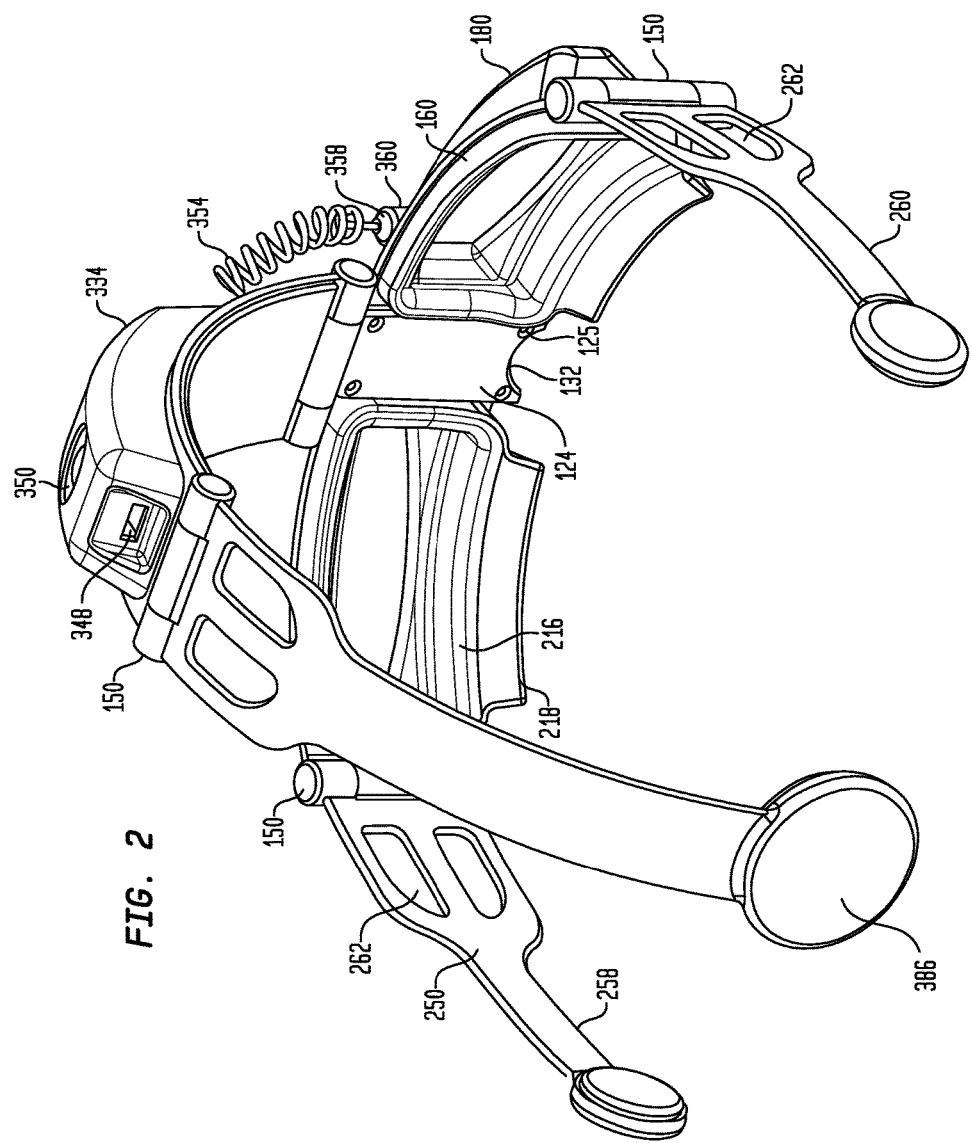
FIG. 2 is a rear perspective view of the embodiment of FIG. 1.
Figure 3:
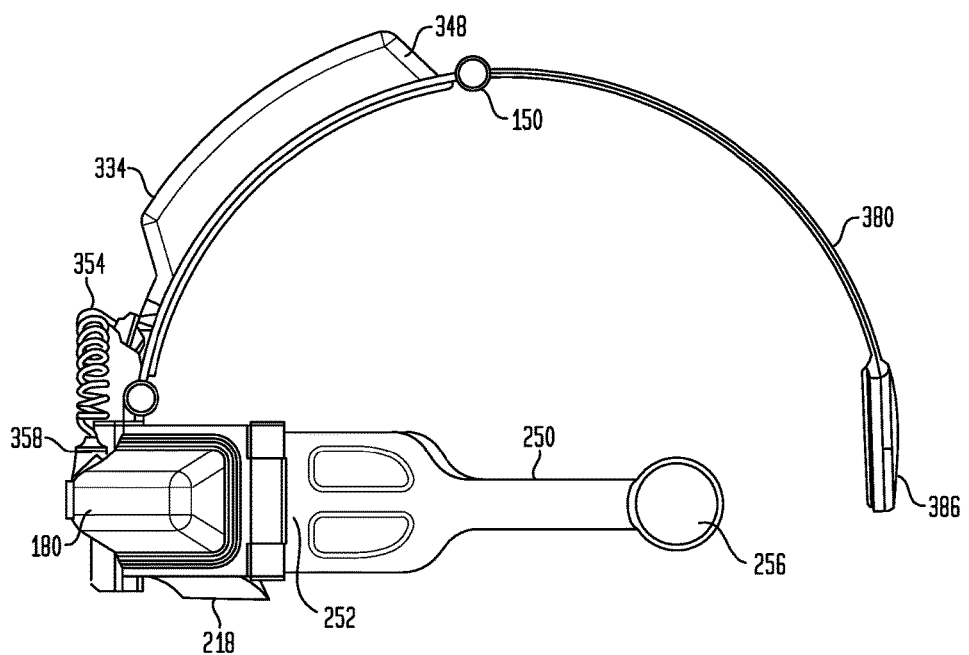
FIG. 3 is a side perspective view of the embodiment shown in FIG. 1, in an open position and the location of the USB port and battery compartment.

Referring now to the drawings, FIGS. 1-3 show an eye-glasses-like eyebrow hair regrowth apparatus 100 embodiment of the present invention. In this embodiment, eyebrow hair regrowth apparatus 100 comprises a frame 110 and a head piece member 300 (FIGS. 1-3, see FIG. 2 for detail).

The frame 110 comprises a central member 120 that separates the light hubs 160, with central member 160 functioning in a manner similar to the bridge of a pair of eyeglasses. Temples 250 are hingedly attached to the light hubs 160. The headpiece member 300 is hingedly attached to the top surface 126 of central member 120 (FIG. 2).

Figure 9:
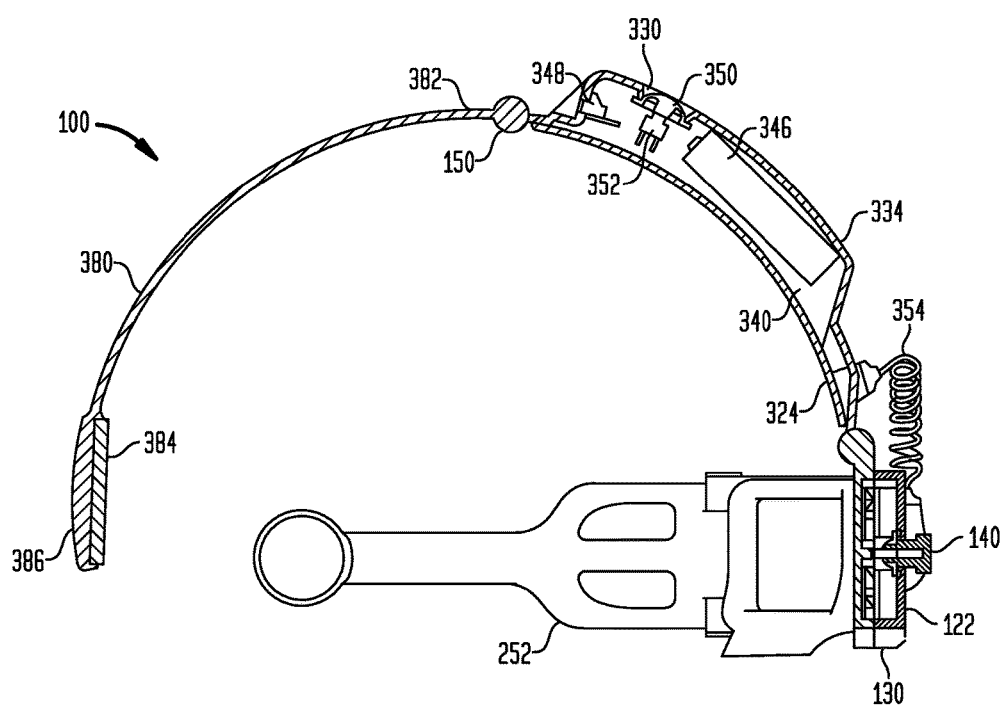
FIG. 9 is a sectional view of the embodiment shown in FIG. 8, taken along line 9-9, and showing structure of the adjustment knob and bars.
Figure 10:
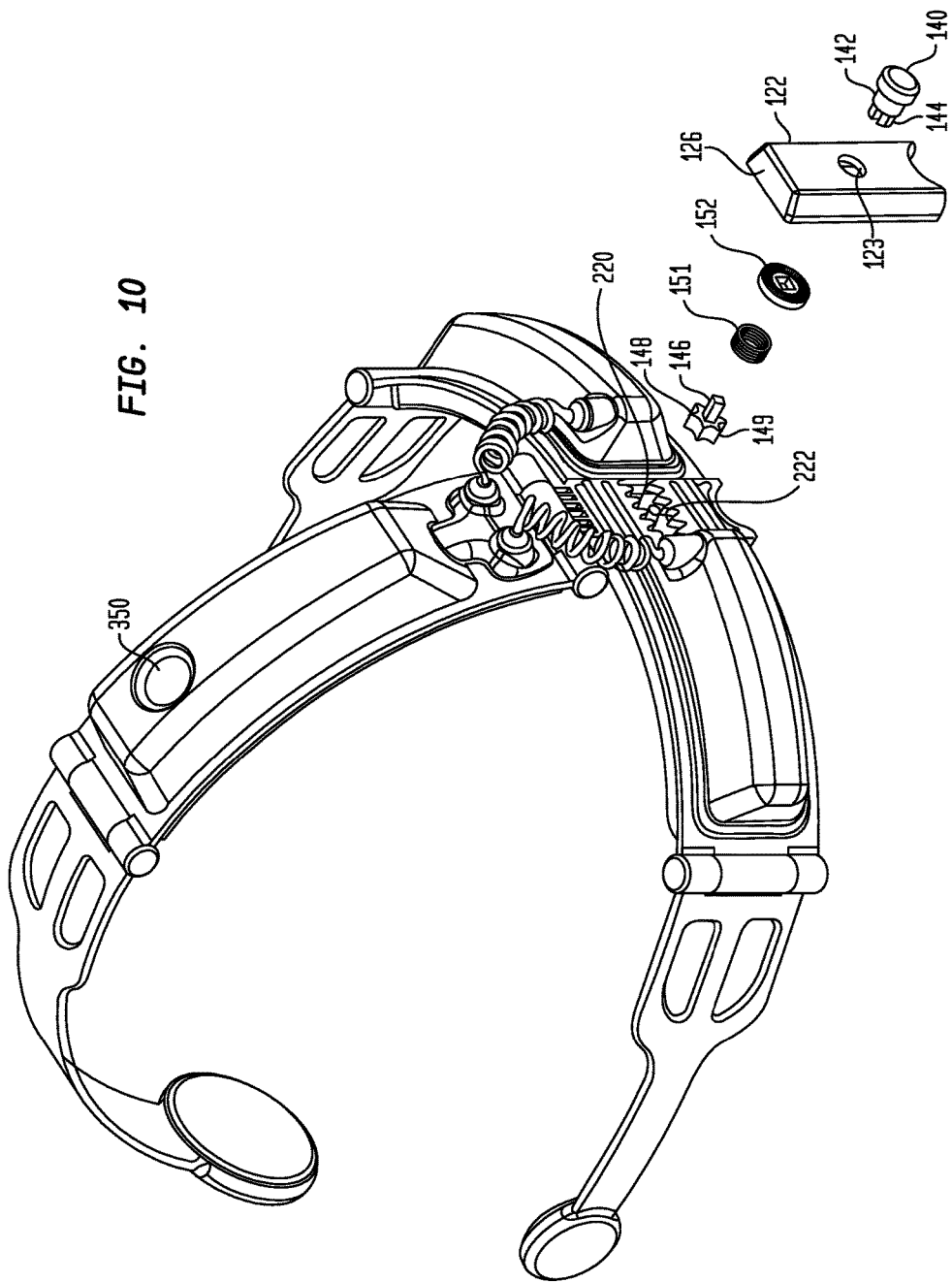
FIG. 10 is an exploded view of the central member 120 showing the eyebrow hub distance adjusting mechanism.

The central member 120 includes a front surface 122, an opening 123, rear surface 124, top surface 126, sidewalls 128, sidewall slit 129, and a bottom wall 130 having an arcuate cutout 132 therethrough (FIGS. 1, 9-10). The rear surface 124 is attached to the central member 120 by fasteners 125. In the embodiment shown in FIG. 2, fastener 125 is a screw, but other fasteners, such as pins, nails, adhesive or welding could also be utilized. The arcuate cutout 132 functions as a nosepiece, allowing a user to position the eyebrow hair regrowth apparatus 100 on the user's nose when the apparatus is being worn. In alternate embodiments a nosepiece having one or more nose guards (not shown) could be positioned proximate the arcuate cutout 132 by a fastener (not shown). Such a fastener could be for example, a screw, but other types of fasteners, such as nails, pins, hook and loop fasteners, welding or adhesives could be used to attach such a nosepiece to the rear surface 124. In alternate embodiments, not shown, the nosepiece could be positioned within the arcuate cutout 132 or mounted on the front surface 122 of the central member 120. The nosepiece can be chosen from any nose guard component used in the manufacture of eyeglasses or similar items, and may include nose guard components having a pad of cushioning material attached thereto. Such cushioning material can include plastic, silicone, felt or foam pads attached to the inside surface (i.e., the side facing the nose) of the nose guard members.

A knob 140 for adjusting the distance between the light hubs 160 is positioned on the front surface 122 of central member 120 (FIGS. 1, 8-10). The knob 140 is attached to a rod 142 that passes through opening 123, and the rod terminates in a receptacle 144 that receives the shaft 146 on which distance adjustment gear 148 is mounted (FIG. 10). A lock spring 150 and a locking disk 152 are positioned on the shaft 146 between the distance adjustment gear 148 and the knob 140. Adjustment knob 140 functions as a spring-loaded push button, such that when one wants to change the distance between the light hubs 160, one pushes the adjustment knob 140 inward and rotates the adjustment knob 140 until the light hubs 160 are in their desired position.

As shown in FIGS. 9 and 10, adjustment gear 148 includes a plurality of teeth 149, and one or more teeth 149 engage with one or more teeth 222 of an adjustment bar 220 for each light hub 160. The adjustment bar 220 is in contact with internal frame 170, and as the adjustment bar is moved, movement of the internal frame 170 results in movement of the light hub 160. As the adjusting knob 140 is rotated, adjustment bar 220 moves through the sidewall slit 123 of the central member 120, enabling movement of the light hubs 160.

When the adjusting knob 140 is rotated in a counter-clockwise manner (clockwise based upon user facing the central member front surface 122), the shaft 142 is rotated, causing the adjustment bars to move towards the gear 146 and inward towards each other. When the adjusting knob 140 is rotated clockwise, the shaft 146 is rotated so that the adjustment bars 220 move away from each other, and the distance between the light hubs 160 increases. Depending upon the strength of the user, the adjustment knob 140 may move with a clicking-type of motion, or, in other embodiments the adjustment knob could move continuously instead of as a click-type movement, or as a ratcheting movement.

The movement of the light hubs 160 is adjustable over a range of about 15 mm, with zero being the smallest distance between the centers of the light hubs 160. Thus, the light hubs 160 can move a distance ranging from about 0 to about 15 mm (maximum of 30 mm between light hubs), a distance of about 1 mm to about 15 mm, (maximum of 30 mm between light hubs), a distance ranging from about 1 mm to about 10 mm (maximum of 20 mm between light hubs), or a distance ranging from about 1 mm to about 5 mm (maximum of 10 mm between light hubs). The sensitivity of the movement of the light hubs can be adjusted in embodiments by changing the gear to another gear with an increased number of teeth compared to the gear used in the embodiment shown.

Figure 7:
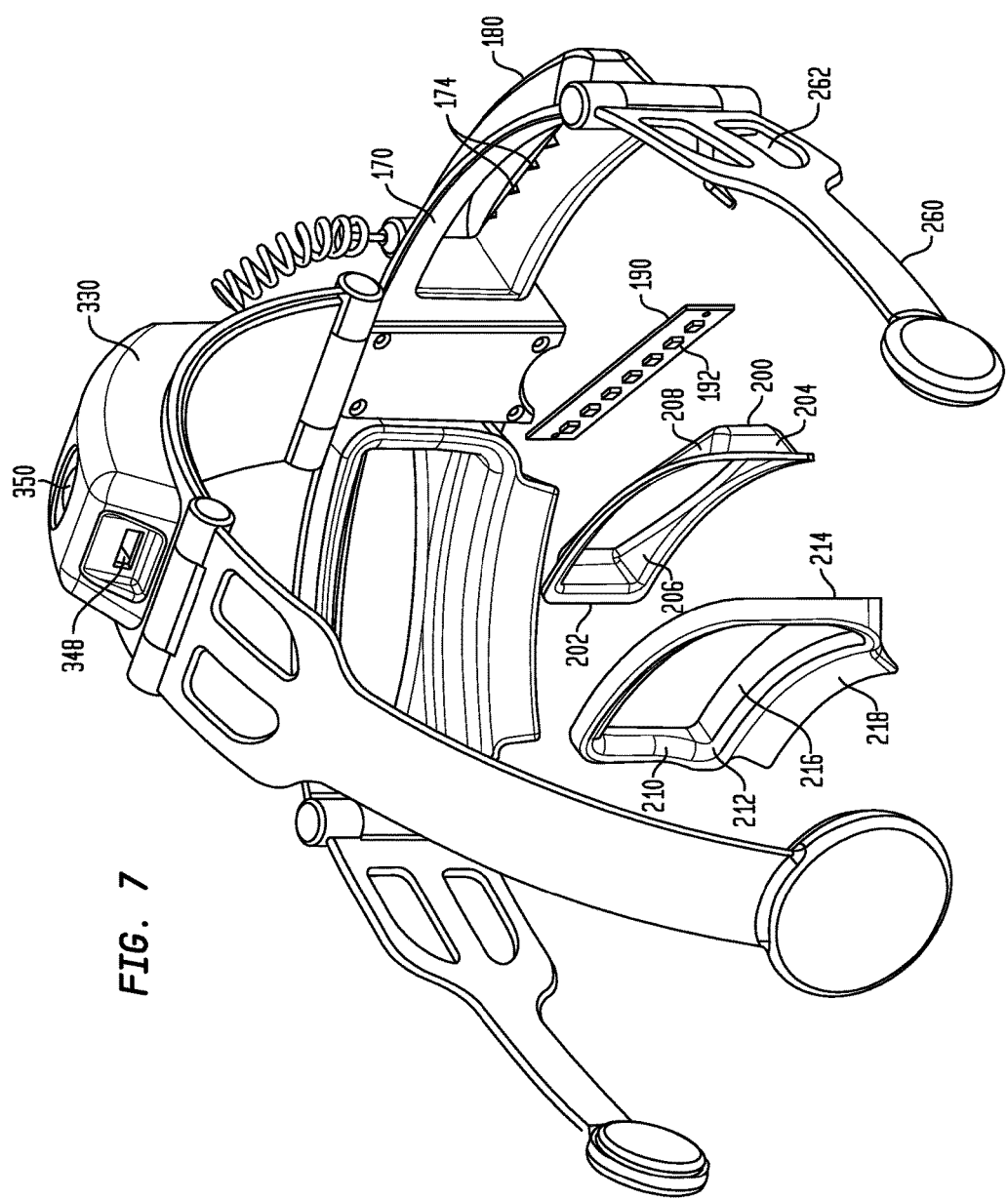
FIG. 7 is an exploded view of the embodiment shown in FIG. 2, showing the structure of the light hubs.
Figure 8:
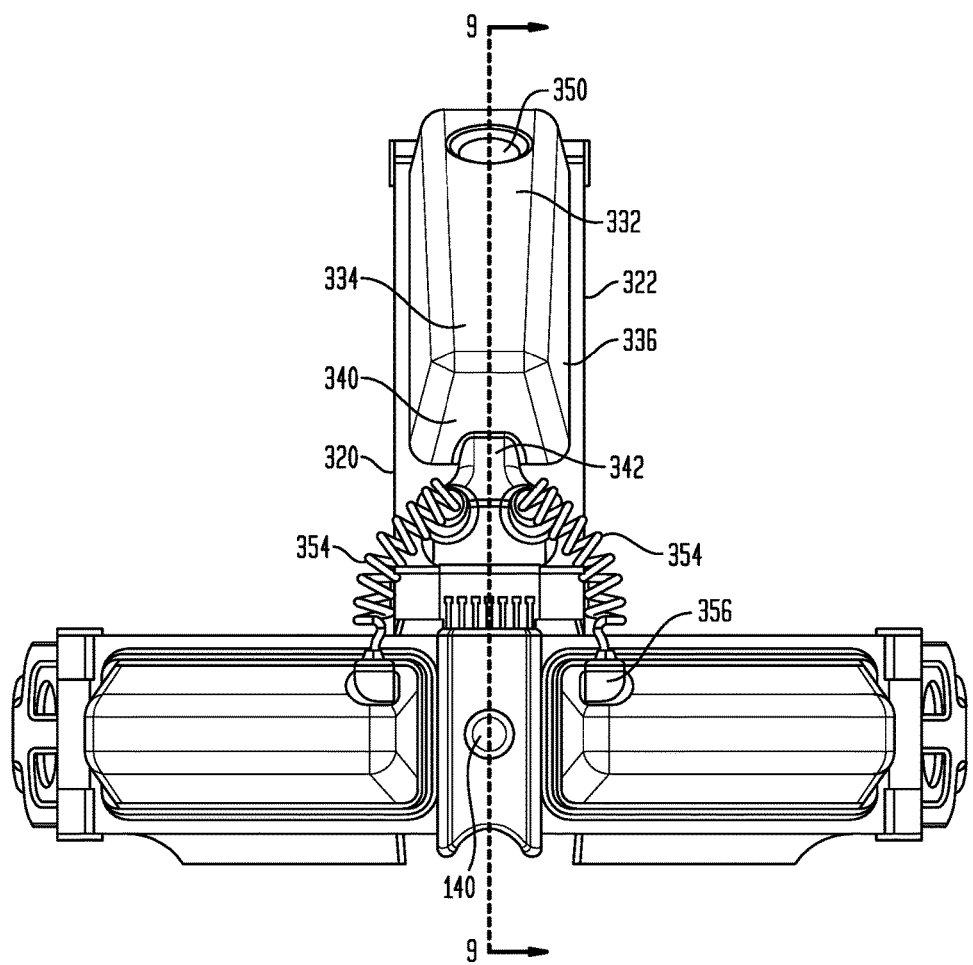
FIG. 8 is a front perspective view of the embodiment shown in FIG. 1, showing the housing and power source.

As shown in FIGS. 2 and 7, the light hubs 160 have an arcuate structure, so that they will fit against the face of a user, and can be adjusted so there are no gaps between the light hub 160 and the user when in use. The light hub body 162 includes a means of being fastened to a hinge 150 on the distal end 166 (distal meaning the end further away from the central member 120) of the light hub 160.

Each light hub 160 includes an assembly comprising an internal frame 170, a front cover 180 and a light subassembly 190 (FIG. 7). The light subassembly 190 may also be referred to Surface-Mounted Diodes ("SMD") Subassembly 190 because the light sources 192 (light emitting diodes) are mounted on the surface of the printed circuit board 194. The light subassembly 190 comprises a printed circuit board ("PCB") 194 that includes the wiring, electronics, and contact points sufficient to enable electrical communication with the light sources of the light subassembly 190, and electrical communication with the power source 330 of the hair regrowth device 100.

The light subassembly 190 is inserted into the internal frame 170, where the contacts (not shown) from the PCB 194 mate with corresponding contacts 174 within the internal frame 170, and which contacts 174 are in electrical communication with the wiring 354 and the power source 330. The front cover 180 can be either a transparent, translucent or opaque material. The front cover 180 covers the components on the back of the PCB 194, and prevents light from leaking out the front of the eyebrow hair regrowth apparatus.

A protective cover 200 is positioned within the internal frame 170 (FIG. 7). Protective cover 200 comprises a body 202, and a shield member 202 attached to the body 202 by sidewalls 204, bottom wall 206 and top wall 208. The shield member 202 is about the same size as the SMD subassembly 190 and when the apparatus is assembled, the shield member 202 is in close proximity to the light sources 192 of the SMD subassembly 190. The protective cover 200 is secured in position by means of a press-fit, adhesive, or a welding or the like, to the internal frame 170. A facial contact member 210 is mounted within the internal frame 170, and is attached to the internal frame 170 by means of a press-fit, or attached by adhesive or ultrasonic welding. Facial contact member 210 comprises a frame having an inside surface 212 and outside surface 214. A layer of padding 216 is attached to the outside surface 214, and covers the outside surface. The padding 216 also includes an eye shield flap 218 that depends from the padding at the bottom of the contact member frame. In the embodiment illustrated, the padding 216 surrounds the entire outside surface 214, but in alternate embodiments, the padding 216 can be mounted so that not all of the entire outside surface 214 is covered. In another alternate embodiment, the distribution of padding can be varied to accommodate the needs of a specific user, for example, with a thick layer padding along the upper portion, and a thinner layer of padding along the lower portion of the facial contact member 216. The padding 216 and eye shield flap 218 enable the eyebrow hair regrowth apparatus 100 to be positioned against the face of a user, provide a seal to prevent light leakage, and when adjusted by the user, provide for a comfortable fit.

The padding 216 may be permanently attached to the facial contact member 210, as seen in the embodiment illustrated. In other embodiments, the padding 216 may be attached using a "weak" adhesive, similar to the pressure-sensitive adhesive used on "sticky notes" commonly utilized in businesses and the home. The padding can be removed after use, or alternatively can be attached by means of hook and loop fasteners to allow for removal and replacement of the padding between users.

The light sources 192 are one or more Light Emitting Diodes (LEDs), one or more infrared LEDs, one or more laser diodes, and/or any other and/or any other suitable light sources. The light sources 192 are individual light emitting diodes ("LEDs") in the embodiment shown in the drawings. In alternate embodiments of the present invention, the light source 192 could be a laser (not shown).

In embodiments of the present invention, the light source can have a wavelength of light ranging from about 600 nanometers ("nm") to about 1200 nm. In the embodiment illustrated in the figures, the wavelength of light emitted from the light sources ranges from between about 650 nm to about 940 nm.

Figure 4:
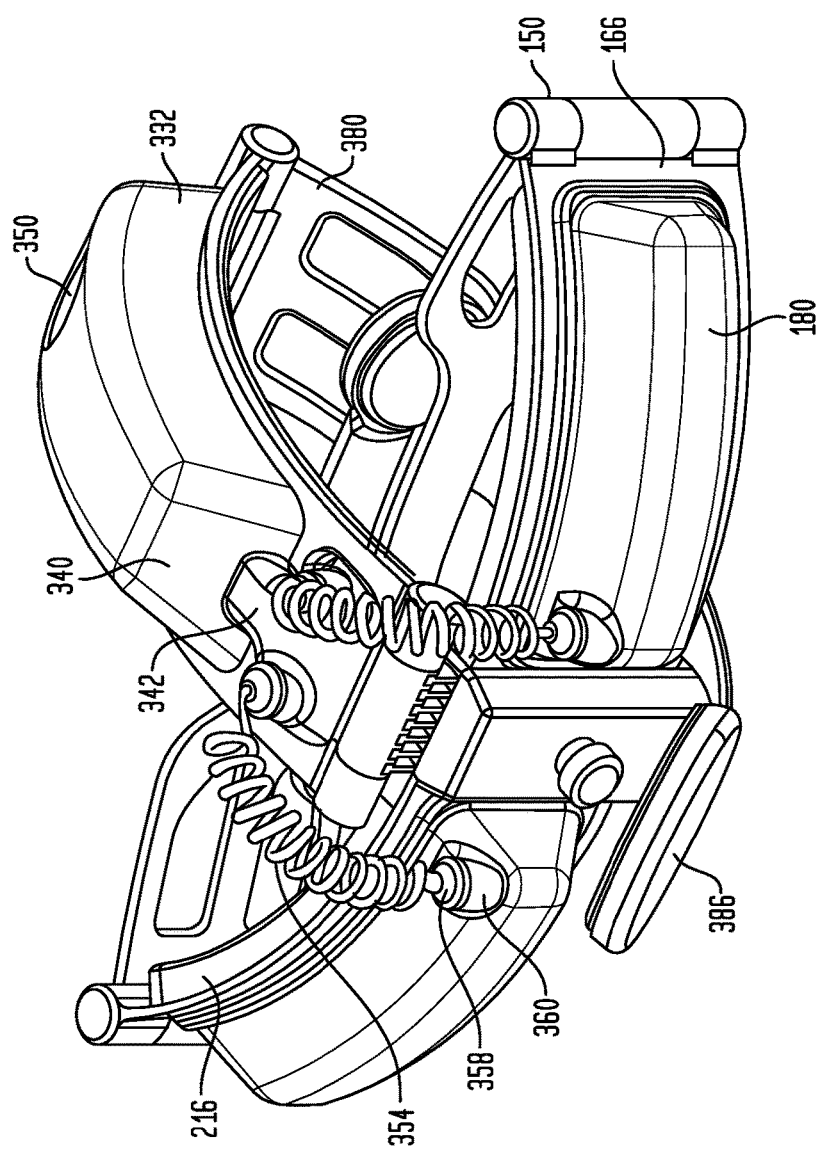
FIG. 4 is a front side perspective view of the embodiment of FIG. 1, in a closed position.
Figure 6:
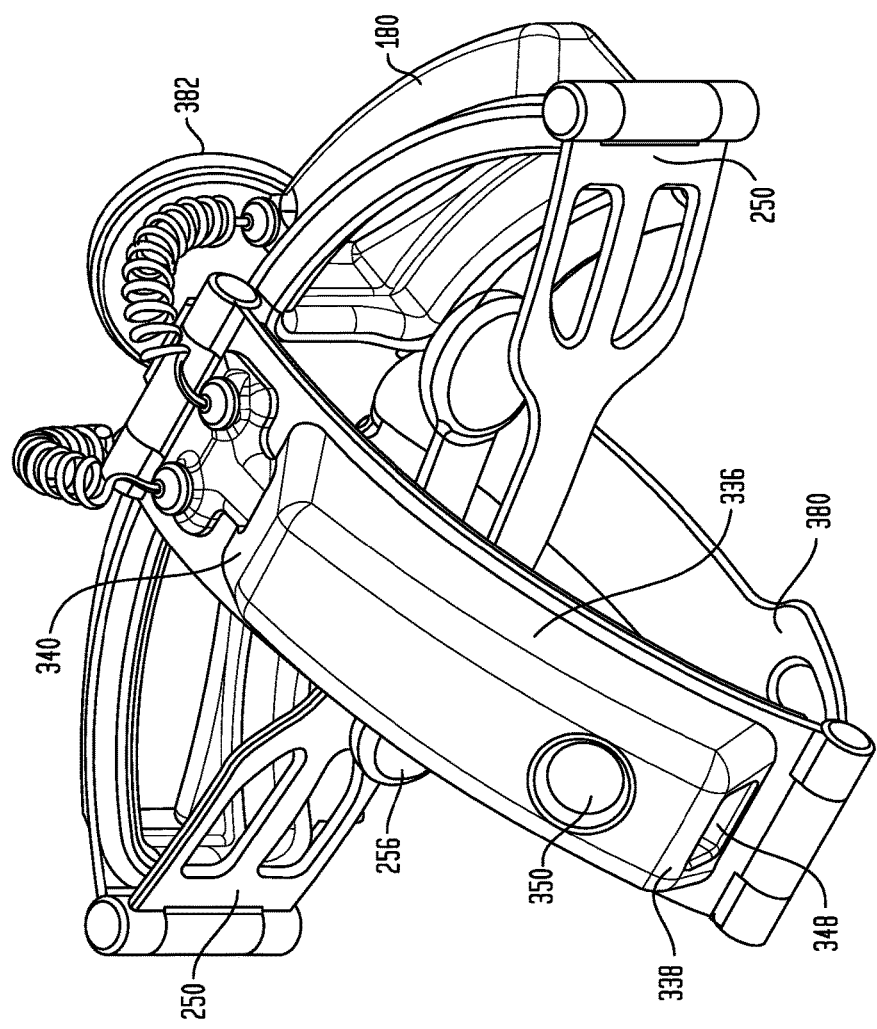
FIG. 6 is a rear perspective view of the embodiment shown in FIG. 4.

The temple first end 252 is pivotably connected to the distal end 166 (distal meaning the end further away from the central member 120) of the light hub 160 by a hinge 150 (FIGS. 1, 6-7). The hinge 150 can be a spring-loaded hinge that is biased such that when pressure is put upon the temple 250, temple 250 will move from the open position (FIG. 2) to the closed position (FIGS. 4 and 6). In other embodiments, the hinge 150 can be a hinge that is not spring loaded or spring-biased, such as commonly used in the manufacture of eyeglasses or comparable items (for example, safety glasses and the like), as known to those of ordinary skill in the art.

Each temple 250 includes a first end 252 and second end 254, the second end 254 being covered by a cushioning material 256 on both its inside surface 258 (side that will face the user's head) and outside surface 260. The cushioning material 256 may extend past second end 254 (FIGS. 1 and 2). The cushioning material 256 can be any type of cushioning material applied to an eyeglass frame, and can include cotton, felt, polyurethane foam, plastic, rubber or silicone or various combinations thereof. The cushioning material aids in keeping the eyebrow hair regrowth apparatus securely and comfortably retained on the user's head during use. In alternate embodiments, the cushioning for the second end 254 may be omitted. In the embodiment shown in the drawings, temples 250 include one or more cutouts 262, to allow for ventilation and for heat generated by the light sources to dissipate. Other embodiments may not include cutouts, or the cutouts 262 may have a different configuration than the temples 250 shown here, and these alternatives are intended to be within the scope of the present invention.

Figure 5:
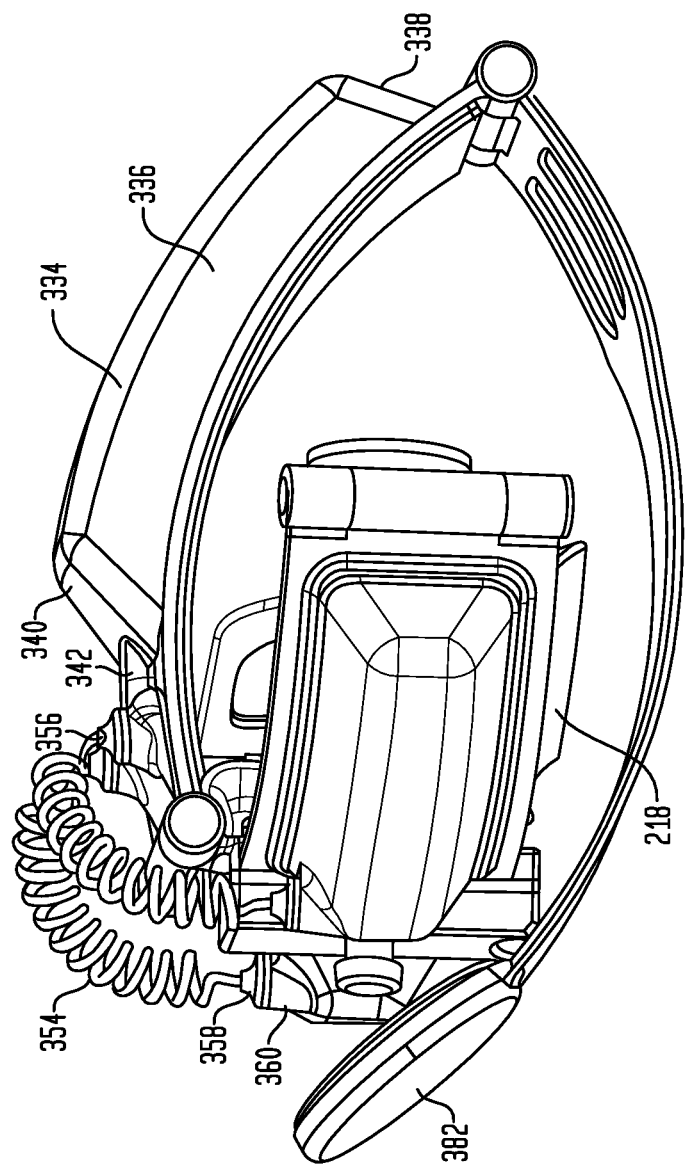
FIG. 5 is a side perspective view of the embodiment shown in FIG. 4.

The headpiece member 300 is pivotably attached to the top surface 126 of the central member 120 by means of a hinge 150 (FIGS. 1, 2 and 5). The headpiece member 300 further comprises a front component 320 and a rear component 380, that are connected to each other by a hinge 150. The second component has a first end 382 that is proximate hinge 150, and a second end 384 which is covered by cushioning 386, in a manner similar to the cushioning 256 on the end of temples 250.

The front component 320 has an outer surface 322 and an inner surface 324. The front component 320 includes a power source 330 for the eyebrow hair regrowth apparatus 100. Power source 330 comprises a housing 332 attached to the front component outer surface 322. The housing 332 includes a removable cover 334 that when opened, exposes a battery compartment 346, and a charging port 348 at one end of the housing 332. The cover 334 can be removed by either a sliding mechanism, held in place by a fastener, or can be retained by prongs at one end. The battery compartment 346 can be sized to hold one or more batteries, such as a lithium ion battery, alkaline battery, silver-oxide, or other type of battery. In the embodiment shown (FIG. 9), the battery compartment 346 is configured to receive a pair of AA-size batteries (not shown). The battery used can be either a disposable battery, or a rechargeable battery, such as a Nickel-Cadmium ("NiCd" or "Nicad"), Nickel metal hydride ("NiMh") or lithium-based battery. For economic and environmental purposes, the eyebrow hair regrowth apparatus 100 will be supplied with a rechargeable battery.

The charging port 348 can be configured to accept a charger such as an AC charger, a DC charger, or accept a Universal Serial Bus ("USB") connector. The embodiment shown (FIG. 9) illustrates a printed circuit board including a micro-USB port and associated electronic components. An on-off switch 350 is mounted on housing 332 and when depressed contacts micro-switch 352 which is in electrical communication with the batteries and charging port 348, and wiring 354 that transmits power and data to the components of the eyebrow hair regrowth apparatus 100.

The wiring 354 divides within housing 332, and exits housing 332 through opening 342 and nipple 356 where it then passes through second nipple 358 to enter channel 360 within each lighting hub 160.

The housing 332 includes a base that is part of the outside surface 322, a cover 334 that includes side walls 336, a top wall 338 and a bottom wall 340 that includes an opening 342 therethrough.

Figure 11:
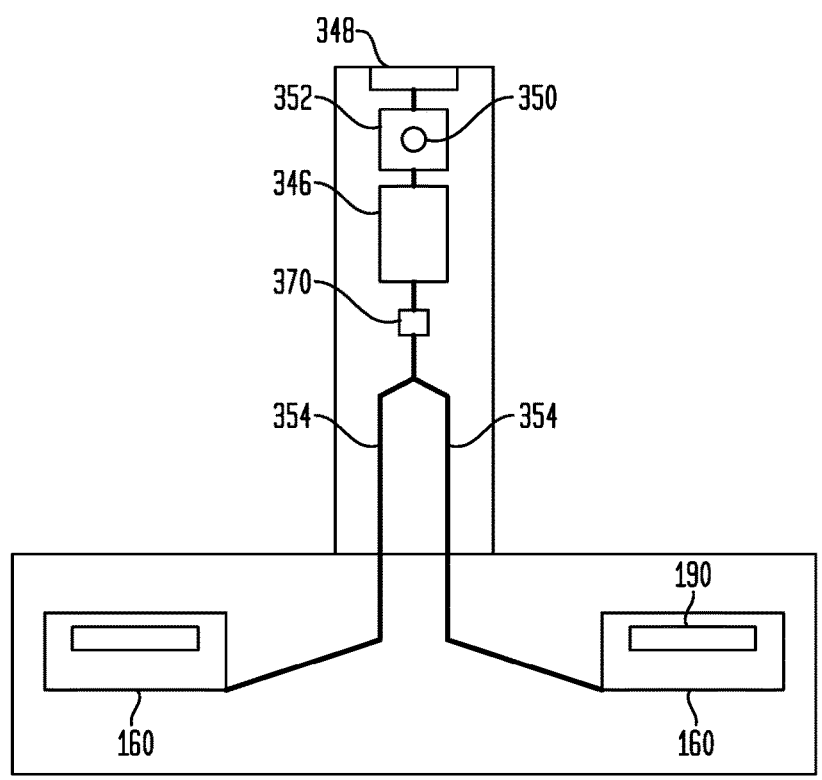
FIG. 11 is a schematic of the electronics connecting the USB port and battery compartment with the light sources of the apparatus shown in FIG. 1.

FIG. 11 is a schematic showing the electronic interactions of the battery compartment 346, the charging port 348, wiring 354 and the microprocessor 370, and from the microprocessor 370 to the light sources 190 within the light hubs 160 of the apparatus 100.

In embodiments, the microprocessor 370 can be programmed during the manufacture of the apparatus 100. The microprocessor 370 will cause light to be emitted in one of several modes by the light sources 192. The first mode is a Continuous Wave mode ("CW") in which the light sources 192 are turned on, either continuously or for a specified period of time, 5 minutes or 10 minutes, for example. A Pulsed Mode ("PM") is the second type, in which the light sources are turned on and off at a frequency of about 50 to about 100 Hz, and with differing power modes (duty cycles) ranging from 25-50%. The apparatus 100 could also be configured to operate as a combination of Continuous Wave and Pulsed Mode, depending upon the needs of an individual user.

In alternate embodiments (not shown) a wireless receiver can be installed in the apparatus and be in electronic communication with the microprocessor 370, and receive signals from a remote source, such as a computer, a handheld device such as a tablet computer or smartphone, to control the frequency and duration of the light sources 190 within the apparatus. An infrared receiver (not shown) could also be installed in alternate embodiments and be in electronic communication with the microprocessor 370, and receive signals from a remote source, such as a computer, a handheld device such as a tablet computer or smartphone, to control the frequency and duration of the light sources 190 within the apparatus.

For use, the wearer opens up the device, brings the head piece member 300 to its open position by removing the rear component 380 out from under the arcuate opening 132 and unfolding both the front and rear components, reference numbers 320 and 380, respectively. The temples 250 are unfolded from behind the frame 111, and brought to their open position. The user then places the eyebrow hair regrowth apparatus 100 on their head in a manner similar to wearing a pair of glasses, allowing the arcuate opening 132 to rest upon their nose, positioning the temples 250 comfortably around their head, and then positioning the head piece member 300 over their head. Using the adjustment knob 140, the user adjusts the position of the light hubs 160 to a position that is comfortable, and enables the light hubs 160 to cover the eyebrow area to be treated. When the apparatus 100 is properly configured by the user, and placed over the eyebrow portion of the user, there should be no gaps between the user and the light hubs 160 on either the top or bottom of the light hubs 160.

When the apparatus 100 is worn by a user, the light emitting devices 192 are directed to an eyebrow portion of the user's face. When turned on, the light emitting devices 192 emit light onto the eyebrow portion of the face. It is noted that the apparatus 100 is configured such that the light emitting devices 192 do not emit light over the eye globe in such a way as to potentially cause harm to the eye globe of the user. Such a position of the apparatus 100 protects the anatomical structures of the eye (such as, e.g., the optic nerve, retina, iris, cornea, aqueous and vitreous humor, etc.) responsible for vision formation from the radiated light.

The user activates the on/off switch 350, and allows the apparatus to perform the programmed light exposure for the specified time period, after which the user turns the switch 350 off, and removes the apparatus 100. The apparatus 100 can be folded as described below, or be left in the open position. The apparatus 100 can be disinfected using an alcohol swab or other disinfectant agent between uses.

When not in use, the eye-glasses-like eyebrow hair regrowth apparatus 100 can be closed, and kept in the closed position for storage (FIGS. 4-6). The temples 250 are folded in a manner similar to that of a pair of eyeglasses, by applying pressure to the second end 254 or to the cushioning material 256, thereby folding the temples 250 inward using hinge 150. The temples 250 should be folded before the headpiece member 300 is folded, to provide a compact configuration. The headpiece member 300 is folded by applying pressure to the rear component 380, thereby causing the rear component to fold along hinge 150 and then for front component 310 to fold along hinge 150, such that rear component 380 becomes positioned underneath the arcuate cutout 132.

Components of the present invention can be manufactured from one or more of a plurality of materials, including metals and/or plastics. Metals can be chosen from aluminum, stainless steel, titanium, chromium, and other metals and/or metal alloys commonly employed in the manufacture of eyeglasses and the like. The shields can be manufactured from a plastic or from an optical glass. Among the types of plastic which can be used are polycarbonate ("PC"), acrylonitrile butadiene-styrene ("ABS"), high impact polystyrene ("HIPS") or a plastic containing a mixture of 14% glass beads and virgin nylon, sold under the trademark of ZYTEL® (registered trademark of EI DuPont de Nemours Co., Wilmington, Del. for resinous virgin plastics in the form of powders and granules).

According to an embodiment, the eyebrow hair regrowth apparatus 100 is configured to target the regrowth of hair lost due to androgenetic and areata forms of alopecia. It is noted, however, that the eyebrow hair regrowth apparatus may be configured to target the regrowth of hair due to other causes of hair loss such as, but not limited to, autoimmune diseases.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. An apparatus to promote the regrowth of eyebrow hair, the apparatus comprising:
   a frame comprising a central member, the central member further comprising a body having a top surface, a bottom surface and a pair of side surfaces;
   a plurality of moveable light hubs attached to the central member side surface, each light hub including a light subassembly including a plurality of light emitting devices and configured to emit light onto the eyebrow region of a user; and
   a temple attached to each light hub, the temple comprising a first end and a second end, the first end being attached to each light hub by a hinge and the second end further comprising padding and configured to support the apparatus on the user's head;
   each central member side surface having an opening therethrough, and the central member further comprising an adjustment mechanism therein, the adjustment mechanism in communication with each light hub,
   the adjustment mechanism being retained within the central member, the adjustment mechanism being a knob including a shaft, a gear on the shaft, the gear interacting with a bar attached to each light hub,
   wherein movement of the adjustment mechanism causes linear movement of the light hubs, thereby altering the interpupillary distance between the light hubs; and
   a control mechanism, further comprising a source of electrical power, the control mechanism being attached to the frame and in electrical communication with the light hubs, whereby after adjustment of the light hubs the apparatus is configured to be positioned on the forehead proximate the eyebrow region of the user; and
   a head piece component, the head piece component being attached to the central member top surface, the head piece component configured to be worn over the head of the user thereby stabilizing the apparatus proximate the eyebrow region.

2. The apparatus as described in claim 1, wherein the control mechanism is attached to the head piece component.

3. The apparatus as described in claim 2, wherein the light hubs comprise an internal frame, a front cover, the light subassembly, a protective cover and a facial contact member, the facial contact member being a subframe mounted within the internal frame, and a means for electrical communication between the light emitting devices of the light subassembly and the source of electrical power.

4. The apparatus as described in claim 3, wherein the light hubs further comprise padding attached to the light hub subframe; and the padding is situated such that at least a portion of the padding is configured to be positioned against the forehead of the user when the adjustment mechanism has been used to position the light hubs on the forehead of the user.

5. The apparatus as described in claim 4, wherein the padding further comprises an eye shield member that extends below the light hub subframe.

6. The apparatus as described in claim 3, wherein the light hubs further comprise a channel, and the means for electrical communication between the light sources of the light subassembly and the source of electrical power passes through the channel.

7. The apparatus as described in claim 3, wherein the light emitting devices are configured to emit light at a wavelength suitable for promoting regrowth of eyebrow hair.

8. The apparatus as described in claim 7, wherein the light emitting devices are light emitting diodes.

9. The apparatus as described in claim 7, wherein the movement of the light hubs ranges from about 0 millimeters to about 15 millimeters.

10. The apparatus as described in claim 2, wherein the source of electrical power source is selected from the group consisting of a battery and a power cable.

11. An apparatus to promote the regrowth of eyebrow hair, the apparatus comprising:
   a frame comprising a central member, the central member further comprising a body having a top surface, a bottom surface and a pair of side surfaces;
   a plurality of moveable light hubs attached to the central member side surface, each light hub including a light subassembly including a plurality of light emitting devices and configured to emit light onto the eyebrow region of a user; and
   a temple attached to each light hub, the temple comprising a first end and a second end, the first end being attached to each light hub by a hinge, the temple second end comprising padding and configured to support the apparatus on the user's head;
   each central member side surface having an opening therethrough, and the central member further comprising an adjustment mechanism therein, and the adjustment member in communication with each light hub, the adjustment mechanism being retained within the central member, the adjustment mechanism being a knob including a shaft, a gear on the shaft, the gear interacting with a bar attached to each light hub, wherein movement of the adjustment mechanism causes linear movement of the light hubs, thereby altering the interpupillary distance between the light hubs;
   a head piece component, the head piece component being attached to the central member top surface, the head piece component configured to be worn over the head of the user; and
   a control mechanism, the control mechanism comprising a source of electrical power and the control mechanism attached to the head piece component and in electrical communication with the light hubs whereby after adjustment of the light hubs the apparatus is configured to be positioned on the forehead proximate the eyebrow region of the user.

12. The apparatus as described in claim 11, wherein the light hubs comprise an internal frame, a front cover, the light subassembly, a protective cover and a facial contact member, the facial contact member being a subframe mounted within the internal frame, and a means for electrical communication between the light emitting devices of the light subassembly and the source of electrical power.

13. The apparatus as described in claim 12, wherein the light hubs further comprise padding attached to the light hub subframe, and the padding is situated such that at least a portion of the padding is configured to be positioned against the head of the user when the adjustment mechanism has been used to position the light hubs proximate the forehead of the user.

14. The eyeglasses-like apparatus as described in claim 13, wherein the padding further comprises an eye shield member that extends below the light hub subframe.

15. The apparatus as described in claim 13, wherein the light emitting devices are configured to emit light at a wavelength suitable for promoting regrowth of eyebrow hair.

16. The apparatus as described in claim 15, wherein the light emitting devices are light emitting diodes.

17. The apparatus as described in claim 16, wherein the movement of the light hubs ranges from about 0 millimeters to about 15 millimeters.

18. A method to promote the regrowth of eyebrow hair, the method comprising the steps of:
   unfolding an apparatus, the apparatus comprising:
   a frame comprising a central member, the central member further comprising a body having a top surface, a bottom surface and a pair of side surfaces;
   a plurality of moveable light hubs attached to the central member side surface, each light hub including a light subassembly including a plurality of light emitting devices and configured to emit light onto the forehead of a user; and
   a temple attached to each light hub, the temple comprising a first end and a second end, the first end being attached to each light hub by a hinge, the temple second end comprising padding and configured to support the apparatus on the user's head;
   each central member side surface having an opening therethrough, and the central member further comprising an adjustment mechanism therein, and the adjustment mechanism in communication with each light hub, the adjustment mechanism being retained within the central member, the adjustment mechanism being a knob including a shaft, a gear on the shaft, the gear interacting with a bar attached to each light hub, wherein
   movement of the adjustment mechanism causes linear movement of the light hubs, thereby altering the interpupillary distance between the light hubs;
   a head piece component, the head piece component being attached to the central member top surface, the head piece component configured to be worn over the head of the user; and
   a control mechanism, the control mechanism comprising a source of electrical power, the control mechanism attached to the head piece component and in electrical communication with the light hubs;
   removing the end of the head piece component from beneath the central member bottom surface and bringing the head piece component to an open position;
   unfolding the temples by applying pressure to each temple to urge each temple away from the rear of the light hubs and into an open position;
   positioning the apparatus on the head of a user by placing the temples proximate the ears of a user, the central member bottom surface resting on or above the nose of the user,
   and positioning the head piece component over the head of the user, whereby after adjustment of the light hubs the apparatus is positioned on the forehead proximate the eyebrow region of the user.

* * * * *